United States Patent [19]

Sting

[11] Patent Number: 4,595,833
[45] Date of Patent: Jun. 17, 1986

[54] MULTIPLE INTERNAL REFLECTION CELL OPTICAL SYSTEM FOR USE IN INFRARED SPECTROPHOTOMETRY OF LIQUID AND FLUIDIZED SAMPLES

[76] Inventor: Donald W. Sting, 358 Turtleback Rd., New Canaan, Conn. 06840

[21] Appl. No.: 534,220

[22] Filed: Sep. 20, 1983

[51] Int. Cl.⁴ .................................... G01N 21/35
[52] U.S. Cl. .................. 250/353; 250/252.1; 250/338; 250/339; 350/620; 356/300
[58] Field of Search .............. 350/294, 620; 356/300, 356/307, 133; 250/338, 343, 339, 353, 252.1, 341

[56] References Cited

U.S. PATENT DOCUMENTS

| | | | |
|---|---|---|---|
| 3,370,502 | 2/1968 | Wilkes, Jr. | 356/133 |
| 3,393,603 | 7/1968 | Harrick | 250/347 |
| 3,681,577 | 8/1972 | Gasiunas | 356/307 |
| 3,817,605 | 6/1974 | Franklin et al. | 350/294 |
| 3,827,059 | 7/1974 | Rambauske | 350/294 |

OTHER PUBLICATIONS

Edmonds, "The Reflaxicon, a New Reflective Optical Element & Some Applications", *Applied Optics*, 12 (8), 8-73, pp. 1940-1944.

*Primary Examiner*—Carolyn E. Fields
*Attorney, Agent, or Firm*—Townsend and Townsend

[57] ABSTRACT

The present invention provides reflaxicon optics for directing infrared radiation from a source into the cone-shaped entry end of a cylindrically shaped internal reflection element, as well as for directing radiation from the cone-shaped exit end of the element towards a detector. Preferably, the contours of the surfaces for the secondary and primary mirrors included in the reflaxicon optics are segments of revolution where the segments are defined as off-axis ellipsoids, in the case where the source infrared radiation is converging, and as cones and off-axis paraboloids, respectively, in the case where the source radiation is collimated. The cylindrically shaped internal reflection element is sealed into a tubular member in order to provide a sample chamber. Liquids and fluidized samples preferably can be passed through the chamber for nondestructive IR analysis.

33 Claims, 12 Drawing Figures

MULTIPLE INTERNAL REFLECTION CELL OPTICAL SYSTEM FOR USE IN INFRARED SPECTROPHOTOMETRY OF LIQUID AND FLUIDIZED SAMPLES

BACKGROUND OF THE INVENTION

This application relates to infrared spectroscopy and, more particulary, to optics included in an infrared spectrophotometer for directing source infrared radiation to a sample under analysis and thence directing resultant radiation as modified by the infrared absorption characteristics of the sample to a detector. Specifically, the invention is directed to an optical system including a cylindrical internal reflection element for incorporation into an infrared spectrophotometer for facilitating the analysis of liquid and fluidized samples, especially aqueous solutions, by infrared spectroscopy.

In the infrared range, practically all organic (and many inorganic) molecules have characteristic spectra that can positively identify them. Unlike chromatographic techniques (and, for that matter, most other analytical methods), infrared (IR) analysis is nondestructive and, with the aid of a computer, produces qualitative and/or quantitative information almost instantly. In addition, IR analysis is a universal technique since it yields spectra on almost any form of a material (solid, liquid, or gas) directly, without changing the material's physical state Much quantitative infrared analysis is conducted by means of Fourier Transform IR analyzers (FTIR's). Computer assisted spectroscopy, including spectroscopy by means of FTIR's, is most important to the analysis of aqueous solutions due to the ability to accurately subtract out the water background.

The known art includes the following for performing analysis of strongly absorbing liquids by means of infrared spectroscopy: very short path length transmission cells; flat-plate multiple internal reflection cells; probes; cylindrical internal reflection elements using Cassegrain optics; rod crystals using refractive lenses; and rod crystals using funnel-shaped mirrors. There are problems with each of these.

IR analyzers have been used for many years for on-stream gas analysis. But liquids, unlike gases, have closely packed molecules, and they absorb infrared radiation strongly. While infrared gas transmission cells commonly are 10 centimeters to several meters in length, liquid transmission cells are typically less than a millimeter, sometimes as short as 10 micrometers, in thickness in order to allow transmission of sufficient infrared radiation to be measurable. Tightly packed molecules in a liquid with water absorption bands make it necessary to go to extremely short path lengths in order to achieve transmission. Flow rates are very limited for flow-through liquid transmission cells. Moreover, flow-through transmission cells have very poor flow characteristics and high back pressures. It is not practical to attempt to pass a process-stream loop continuously through such flow-through transmission cells. Very short path length transmission cells are difficult to fill, especially in the case of a high viscosity liquid. They are difficult to clean, and cleaning takes a significant amount of time. Slight changes in pressure and/or temperature cause changes in path length. Path lengths change with viscosity and over time. Transmission cells often leak. Usually non-inert amalgam metal transmission cells are used.

In recent years, a technique called multiple internal reflection (MIR) has come into use, which overcomes the need for very short path length transmission cells. Originally developed for obtaining infrared spectra on solid surfaces, the MIR technique also can be used for strongly absorbing liquids, because the effective path lengths generated in MIR cells are typically in the 1- to 50-micrometer range.

The MIR technique makes use of the fact that when infrared radiation propagating within a transparent medium is reflected internally from a surface, a portion of the radiation projects slightly beyond the reflecting surface. When a rare medium, such as air, is in contact with the surface, there is little interference with or attenuation of the infrared radiation. But, if an absorbing liquid is brought into contact with the surface, infrared radiation is absorbed at those wavelengths at which the liquid normally absorbs (as in a transmission cell). Therefore, the reflected infrared radiation carries information that indicates absorption by the sample in the region of the reflecting surface. Since the infrared radiation extends only a few micrometers into the sample, any sample beyond that distance has no effect on the measurement.

Typically, the optical element through which the infrared radiation propagates is a flat plate with polished parallel surfaces and angled ends. A sample is placed in contact with one or both of the reflecting surfaces. Absorption at specific wavelengths then is measured to provide composition information for the sample.

The flat-plate configuration has limitations, however, in that the rectangular shape of the flat-plate element makes it difficult to seal the element into a leak-tight chamber without causing substantial optical interference from the seal. IR analysis using the flat-plate configuration is also characterized by the following additional difficulties. FTIR beams are round, and, consequently, slight movements cause substantial differences in infrared radiation throughput. Good seals are difficult to obtain, especially if pressure is present. Slightly different alignment can cause sampling of a different area. Either the entire MIR cell or the flat-plate element must be removed to clean, thereby resulting in a need to re-align.

IR analysis using probes is difficult because tolerances on probes are extremely critical. Also, good seals are difficult to effect on probes, because they generally have a square cross-section.

An MIR optical element constructed from a cylinder instead of a flat plate is disclosed in Paul A. Wilks, Jr., "Sampling Method Makes On-Stream IR Analysis Work," *Industrial Research & Development*, September, 1982. Polished cone-shaped ends on the cylindrical element perform the same function as the angled ends on a flat-plate element.

The cylindrical configuration has significant advantages over known MIR cells having flat plates. The cylindrical element can be sealed into a sample chamber capable of withstanding several atmospheres of pressure, yet a sample can flow freely through the chamber. Furthermore, the seal has only a small area of contact with the cylindrical element; therefore, the seal has little effect on the infrared radiation within the element. Additionally, the only materials exposed to the sample are the glass (or stainless steel) envelope which surrounds the cylindrical element, the O-rings generally used for sealing, and the element itself, which typically is constructed from a material having a high index of refraction, such as zinc sulfide or sapphire. The MIR cell can be flushed with caustic solution or with organic solvents for cleaning. For aqueous solutions, flushing with water is sufficient for cleaning.

The Wilks article discloses large-aperture optics included in an IR analyzer, which optically couple with the cone-ended cylinder. The optics include a two-mirror configuration. Infrared radiation passes through a hole in a first mirror and strikes a second mirror with central rays at an angle of 45°. The outside polished surface of the first mirror defines the maximum angle, and the diameter of the hole defines the minimum angle, of the edge rays. The radius of curvature of the second mirror is selected so that the infrared radiation is reflected to the first mirror as a beam that is approximately collimated. Since the first and second mirrors are identical, the first mirror forms an image of the source a short distance through a hole in the second mirror.

When the 45° cone-shaped end of the cylindrical element nearer the source end of the IR analyzer is placed so that the image of the source is just inside the cone, the infrared radiation which enters the element is at an average angle perpendicular to the cone face. Therefore, the infrared radiation reflects down the cylindrical element at an average internal angle of 45°.

When the infrared radiation reaches the cone-shaped end of the cylindrical element nearer the detector end of the IR analyzer, the radiation emerges as an expanding ring of radiation with the same angular spread as the radiation which enters the element. Consequently, a pair of mirrors identical to those at the source end of the IR analyzer can be used for focusing the infrared radiation onto the detector.

The optics disclosed in the Wilks article, however, are configured for a stand-alone IR analyzer in which the infrared radiation from the source is highly divergent. Consequently, the optics, although they have proven useful in the case of divergent sources, are not effective in the case of a collimated or convergent beam, such as in the case of an existing center focus or edge focus IR analyzer.

Other optical systems have been used in combination with an MIR cell having a cylindrical element for use with collimated or convergent beams. However, the optics have proven inadequate for various reasons.

One known MIR cell having a cylindrical element includes Cassegrain optics. Unfortunately, Cassegrain optics have the difficulty that the physical size of the optics is very large, and, consequently, the MIR cell is unuseable in many IR analyzers. Cassegrain optics are very difficult to align and use due to size and magnification. In addition, the use of Cassegrain optics results in significantly lower infrared radiation throughput due to obscuration loss from a necessarily large secondary mirror. (Conventional Cassegrain optics design assumes a continuous secondary surface.)

Another known MIR cell having a cylindrical element includes optics in the form of refractive lenses as disclosed in Wilks, Jr., U.S. Pat. No. 3,370,502. However, lenses have unacceptable inherent losses, as well as a limited frequency range. Furthermore, lenses have a wide variation in angle of incidence, which creates significant sampling problems.

Also, a known MIR cell includes optics comprising funnel-shaped mirrors (single mirror elements) in combination with a cylindrical element as disclosed in Wilks, Jr., U.S. Pat. No. 3,370,502. This configuration is indicated to be particularly suited for incoming parallel rays (collimated source infrared radiation), such as in spectrophotometers. However, the funnel-shaped mirror optics undesirably have a wide variation in angle of incidence. Furthermore, difficulties arise in focusing the emergent infrared radiation onto the detector.

The optics used in the past in combination with a cylindrical element for concentrating and/or collecting infrared radiation as part of an MIR cell in infrared spectroscopy with collimated or converging source radiation, such as present in the sample chamber of an FTIR spectrophotometer, have not met with any degree of success. The present invention provides optical means which in combination with a cylindrically shaped internal reflection element forms an optical system for an MIR cell which not only overcomes the problems encountered with similar cells in the past, but produces a throughput of two to six times greater than known MIR cells having a similar internal reflection element, when the infrared radiation source is a collimated or convergent beam with a circular or near circular cross-section.

SUMMARY OF THE INVENTION

The present invention provides an optical system for an MIR cell including a cylindrically shaped internal reflection element. Central to the optical concept is optical means provided by the invention for optically coupling a source of infrared radiation from collimated to f number 1 to one end of a cylindrically shaped internal reflection element, preferably a double-ended pencil-shaped rod of crystalline material, which samples liquids and fluidized samples via internal reflection, and for optically coupling the other end to a detector in a manner so as to provide optimum optical throughput. A maximum of infrared radiation is pumped through the cylindrically shaped internal reflection element for high signal-to-noise ratio sampling. The configuration of the MIR cell, including the cylindrically shaped internal reflection element in combination with the optical means in accordance with the invention, maximizes signal-to-noise by reflecting substantially all infrared radiation emanating from the element to the detector. The multiple internal reflection cell in accordance with the invention can be configured as an accessory which can easily be used for aqueous solution IR analysis, for example, with most commercially available FTIR spectrophotometers. The multiple internal reflection cell in accordance with the invention maintains the same apparent focal plane in the IR analyzer. That is, infrared radiation from the source is transferred through the multiple internal reflection cell in such a way that the radiation emerging from the cell appears to emanate from the center or edge focal plane of the sample compartment of the IR analyzer.

In accordance with the invention, optics are provided in combination with a cylindrically shaped internal reflection element forming an optical system for a multiple internal reflection cell, the optics comprising: a first optical means responsive to radiation from collimated to f number 1 from a source of infrared radiation for focusing the radiation on an entry end of the element at an angle of incidence conducive to transfer of substantially all the radiation to the element; the radiation transferred to the element being multiply internally reflected through the element from the entry end to an exit end of the element; and a second optical means responsive to substantially all radiation emanating from the exit end of the element for transmitting the radiation in a pattern for optimum throughput to a detector. The throughput attainable is at least 15% to 35% of the open beam throughput (infrared radiation through the IR analyzer without a cell and/or sample present).

The invention provides optical means preferably in the form of reflaxicon optics for directing infrared radiation into the entry end of the cylindrically shaped internal reflection element, as well as for collecting radiation from the exit end of the element. Preferably, the contours of the surfaces for the primary and secondary mirrors included in the optical means are segments of revolution where the segments are defined as off-axis ellipsoids in the case where the source infrared radiation is converging. In the case where the source infrared radiation is collimated, the contours of the surfaces for the primary and secondary mirrors are segments of revolution where the segments are defined as off-axis paraboloids and cones, respectively, or vice versa.

The optical means in accordance with the invention provides the ability to couple infrared radiation in a ring to and from a cone shape at a near normal angle of incidence at all points on the cone. The optical means directs, as well as collects, the infrared radiation within a small space (radial from the axis of the cylindrically shaped internal reflection element). The optical means yields high infrared radiation throughput, especially for radiation of f number 3.0 or greater.

One embodiment in accordance with the invention includes a cylindrically shaped internal reflection element consisting of a crystalline material having a relatively high index of refraction. Whereas a large number of crystalline materials, lengths, diameters, and cone angles can be used for providing different effective path lengths for the infrared radiation through the sample, one embodiment in accordance with the invention incorporates zinc selenide (ZnSe) material ¼" diameter by 3¼" long or ⅛" diameter by 1⅝" long with a 45° cone angle (i.e., 90° cone) so as to yield effective path lengths which allow for linear subtractions (i.e., governed by the Beer-Lambert Law) for aqueous solutions and/or other highly polar solvents where a very short effective path length is required in order to see past the highly absorbing solvent bands. The cylindrically shaped internal reflection element is preferably sealed within a coaxial tubular member so as to form a sample chamber between the element and the tubular member. The inclusion of a cylindrical rod of crystalline material as the internal reflection element allows the use of O-rings for effective seals. Liquids and fluidized samples preferably can be passed through the sample chamber.

The multiple internal reflection cell in accordance with the invention has proved to have significant benefits over known MIR cells. The optical system has proved to be highly stable and easy to align in IR analyzers, such as FTIR spectrophotometers. High quality spectra of samples dissolved in water are achieved with relative ease. Quantitative IR analysis of aqueous based samples is easy to perform and calibrate. There is a significant reduction in sampling error due to the ease of the IR analysis procedure. A tremendous savings in time results. Many IR analyses can be performed which were previously considered impossible (or at least extremely difficult) to perform. IR analysis of catalytic reactions, for example, now can easily be performed. Known MIR cells caused such IR analysis to be very difficult. High pressure and high temperature IR analysis also can now easily be performed.

The optical means in accordance with the invention focuses from the source and transmits to the detector a much higher percentage of the total available infrared radiation than have MIR cells including Cassegrain optics. Comparisons with known MIR cells including a cylindrical element indicate the multiple internal reflection cell in accordance with the invention provides a signal-to-noise improvement of 2 to 6 times. The infrared radiation throughput is significantly higher.

BRIEF DESCRIPTION OF THE DRAWINGS

The above and other features and the concomitant advantages of the present invention will be better understood and appreciated by those skilled in the art in view of the description of the preferred embodiments given below in conjunction with the accompanying drawings. In the drawings:

FIG. 3, comprising

DESCRIPTION OF THE PREFERRED EMBODIMENTS

In order to make use of internal reflection as a sampling method for IR analysis, the infrared radiation preferably enters the internal reflection element at an average angle perpendicular to the entrance face and is reflected internally at the correct angle of incidence toward the next reflecting surface. Consequently, when the infrared radiation reaches the end of the internal reflection element, the radiation emerges with approximately the same angular spread as the radiation which entered the element.

Figure 1:
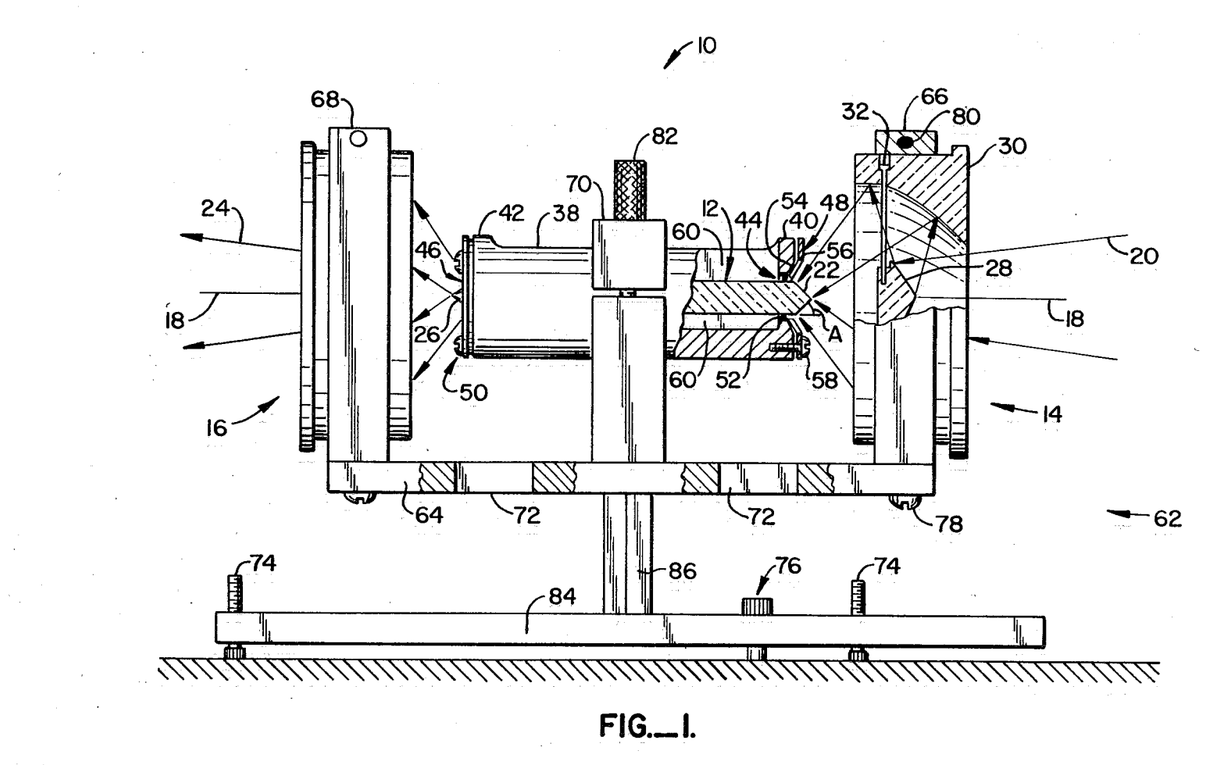
FIG. 1 is a partially cutaway side elevational view of one embodiment of the multiple internal reflection cell in accordance with the invention.

Referring to FIG. 1, a multiple internal reflection cell 10 in accordance with the invention includes a cylindrically shaped internal reflection element 12 in combination with first and second optical means or infrared radiation focusing means 14 and 16, respectively, in the form of reflecting optics located at the respective ends of the element, the combination of the element and the first and second optical means comprising the optical system of the cell. The cylindrically shaped internal reflection element 12 and first and second optical means 14, 16 preferably have a common axis, hereinafter referred to as the optical axis 18 of the multiple internal reflection cell 10. On-axis optics offer simplicity of configuration through the elimination of additional transfer optics.

The first optical means 14 is the input end optics which are used for focusing infrared radiation 20 from a source (not shown) onto the entry end 22 of the cylindrically shaped internal reflection element 12 near the source. The first optical means 14 is configured to accept the full or nearly full infrared radiation 20 from the source with minimal loss in view of the following factors. Firstly, the infrared radiation 20 from the source directed onto the entry end 22 of the cylindrically shaped internal reflection element 12 is directed at a prescribed angle, plus or minus an acceptable deviation, so as to assure total internal reflection for the radiation entering the element. Furthermore, IR analyzer sample compartments are limited in size due to other considerations, and, therefore, the first optical means 14 needs to be compact in order to allow the multiple internal reflection cell 10 to easily fit into the sample compartments of different commercially available FTIR spectrophotometers. Moreover, different IR analyzers have different optical configurations which result in differences in position of focus (if not collimated), size of image at the focus, and f number of the converging and/or diverging infrared radiation through the FTIR spectrophotometer sample compartment. Also, the area of the face of the entry end 22 of the cylindrically shaped internal reflection element 12 is not necessarily (and is usually not) the same area as the cross-section of the infrared radiation 20 from the source. Additionally, demagnification (or magnification) of the infrared radiation 20 from the source can be needed in order to effect minimal vignetting. Furthermore, the cylindrically shaped internal reflection element 12 can be constructed from various materials due to different analytical requirements, such as the acidity or basic nature of the sample, wavelengths of interest, and path length of infrared radiation through the sample. Lastly, different sizes for the cylindrically shaped internal reflection element 12 can be used due to analytical considerations such as surface area or total sample available (or required).

The second optical means 16 is the output end optics which are used for transmitting infrared radiation 24 emitted from the exit end 26 of the cylindrically shaped internal reflection element 12 in order to direct the radiation towards detector optics or a detector (not shown). The second optical means 16 is configured giving due consideration to the following. Firstly, the infrared radiation 24 emanating from the exit end 26 of the cylindrically shaped internal reflection element 12 is emitted mostly at the angle(s) at which the radiation enters the element. Deviations occur due to scattering and misalignment; however, the infrared radiation 24 emitted from the exit end 26 of the cylindrically shaped internal reflection element 12 largely acts as an image of the radiation 20 from the source. Furthermore, FTIR spectrophotometer sample compartments are limited in size due to other considerations, and, therefore, the second optical means 16 needs to be compact in order to allow the multiple internal reflection cell 10 to easily fit into the sample compartments of different commercially available IR analyzers. Moreover, different IR analyzers have different optical configurations which result in differences in position of focus (if not collimated), size of image at the focus, and f number of the converging and/or diverging infrared radiation through the FTIR spectrophotometer sample compartment. Also, focusing can be needed due to slight differences in placement and IR analyzer configuration. Additionally, angular movement is needed in order to direct the infrared radiation 24 emanating from the exit end 26 of the cylindrically shaped internal reflection element 12 properly onto detector optics or the detector. Furthermore, the area of the face of the exit end 26 of the cylindrically shaped internal reflection element 12 acts as a source image, and, therefore, the infrared radiation 24 emanating from the exit end of the element must be redirected in such a way to act as the original source. Also, magnification or demagnification can be needed. Additionally, manufacturing cost benefits can result by constructing the first and second optical means 14, 16 symmetrically. Finally, different sizes for the cylindrically shaped internal reflection element 12 can be used due to analytical considerations such as surface area or total sample available (or required).

Figure 2:
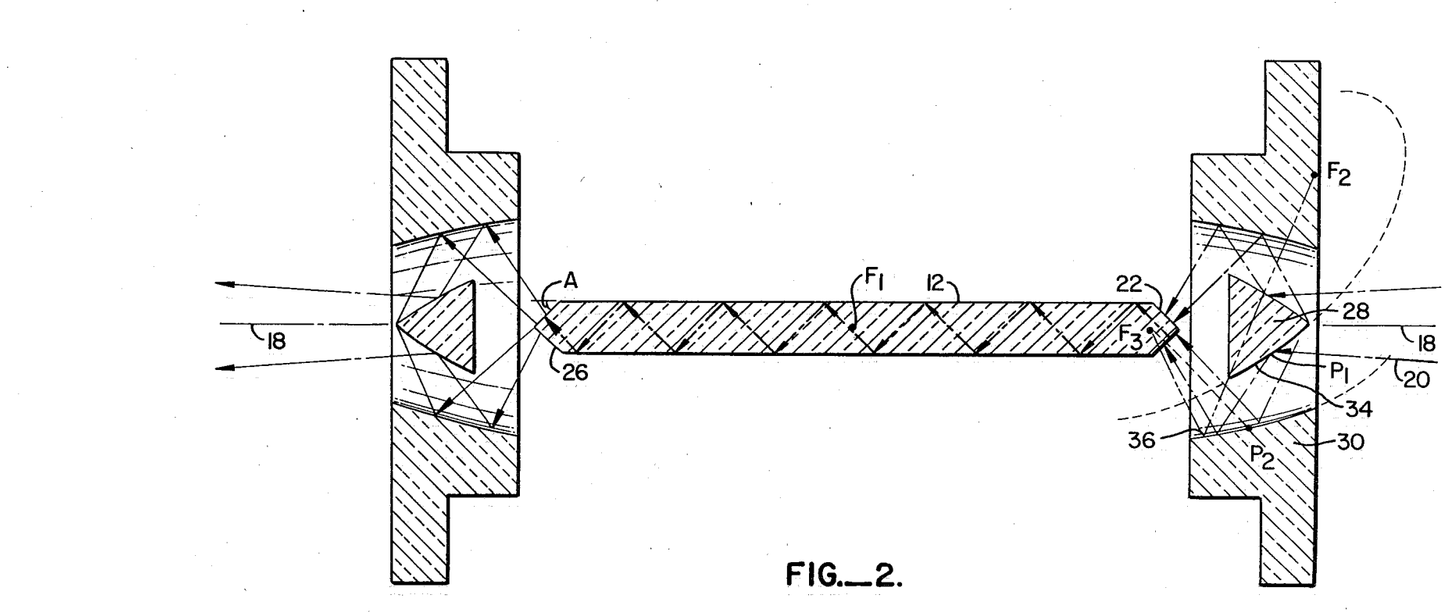
FIG. 2 is a schematic diagram of the optical system in accordance with the invention included in the multiple internal reflection cell shown in FIG. 1.

As shown in FIGS. 1 and 2, the cylindrically shaped internal reflection element 12 is preferably a rod of crystalline material having a cone-shaped entry end 22 and a similarly shaped exit end 26. Different crystalline materials require different face angles if the same effective path lengths are desired. Different crystalline materials are used in order to resist different chemical substances and/or analyze different wavelength regions. The cone angle A shown in FIGS. 1 and 2 can be any angle so long as the angle is not so great of an angle as to cause the number of reflections to be too few in number, thereby resulting in reduced sensitivity, or so small of an angle as to cause transmission rather than total internal reflection.

A preferred material for the cylindrically shaped internal reflection element 12 is zinc selenide (ZnSe) due to its insolubility in water, wide transmission range in the infrared region including the useful water region, resistance to a wide range of chemicals, and relatively high refractive index (2.4) which renders it an efficient internal reflection element material. The preferred cone angle A is 45° for ZnSe. The ratio of L/D (L=length, D=diameter) is preferably 10 to 14. Two preferred sizes are shown in Table I.

TABLE I

| Crystal I | L = 3.00"–3.25"  A = 45° |
| | D = 0.25" material = ZnSe |
| | L/D = 12–13 |
| Crystal II | L = 1.50"–1.625"  A = 45° |
| | D = 0.125" material = ZnSe |
| | L/D = 12–13 |

In the case of a 45° cone angle A and the infrared radiation 20 entering the entry end 22 perpendicularly to the face, L/D approximates the number of internal reflections the radiation makes against the cylindrical wall (area) of the cylindrically shaped internal reflection element 12. At a 45° angle of incidence to the reflecting surface, the depth of penetration is about 1.5 micrometers per reflection. Consequently, a multiple internal reflection cell 10 with 8 to 10 reflections has effective path lengths in the correct range for most aqueous solution studies. Other materials, such as Ge, Si, sapphire, AgBr, AgCl, KRS-5, HDPE, ZnS, as well as others, can be used. The path length can be varied by the use of different internal reflection materials; however, the angle A is typically selected in order to yield appropriate path lengths for analysis of aqueous solutions.

Figure 3A:
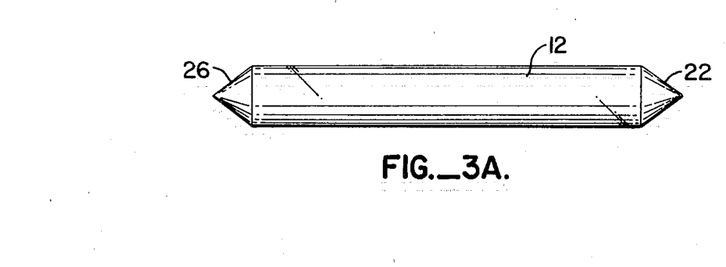
FIGS. 3A, 3B, 3C, 3D, and 3E, illustrates various alternative configurations for a solid cylindrically shaped internal reflection element included in the multiple internal reflection cell shown in FIG. 1.
Figure 3B:
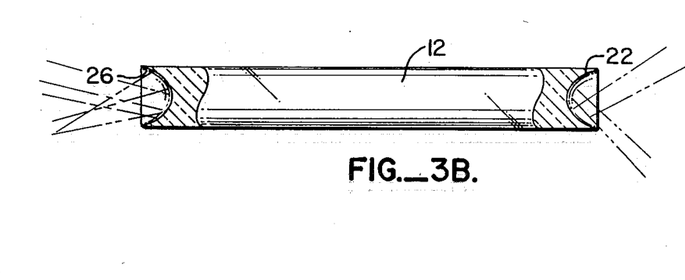
Figure 3C:
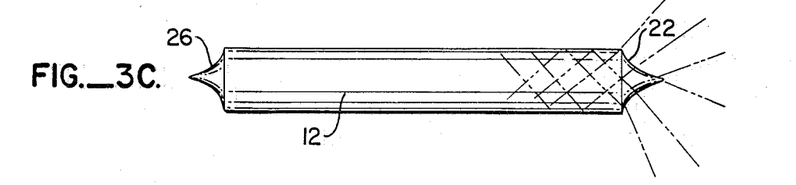
Figure 3D:
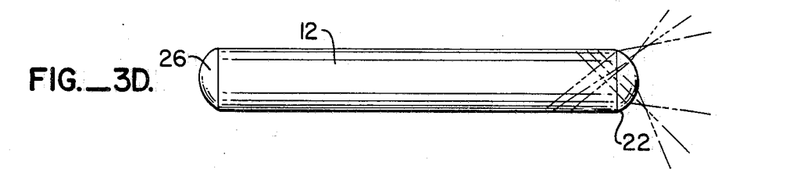
Figure 3E:
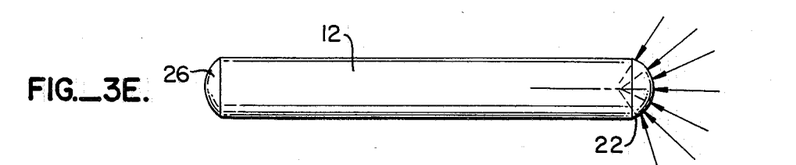

The rod of crystalline material which comprises the cylindrically shaped internal reflection element 12 is preferably a cylindrical shape with the entry end 22 and the exit end 26 of cone shape as better shown in FIG. 3A. The alternative shapes for the cylindrically shaped internal reflection element 12 shown in FIGS. 3B through 3E can result in infrared radiation throughput benefits. However, manufacturing considerations can limit their desirability. The angle of incidence on the entry end 22 of each cylindrically shaped internal reflection element 12 shown in FIGS. 3B through 3E is identical to the angle of incidence for the double-ended pencil-shaped element shown in FIG. 3A for the same crystalline material, for example, 45° in the case of ZnSe.

Figure 4:
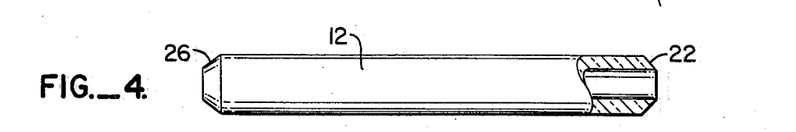
FIG. 4 illustrates a configuration for a tubular cylindrically shaped internal reflection element alternatively included in the multiple internal reflection cell shown in FIG. 1.

As shown in FIG. 4, the crystalline material which comprises the cylindrically shaped internal reflection element 12 can be tubular in order to change the effective path length and/or the method for causing sample contact with the element (i.e., the inside of the element can be the contact surface). Favorable fluid flow conditions can result.

Referring again to FIG. 1, the first optical means 14 preferably includes a reflecting cone or secondary mirror 28, a reflecting toroid or primary mirror 30, and a spider post 32 for mounting the reflecting cone with respect to the reflecting toroid for efficient throughput of the infrared radiation 20 from a collimated to f number 1 source of radiation to the cylindrically shaped internal reflection element 12. The configuration of the first optical means 14 is similar to reflaxicon optics used as beam expanders in conjunction with lasers.

While there are many combinations of crosssectional shapes for the reflecting cone 28 and reflecting toroid 30, the preferred shapes are derived in view of the following considerations. With regard to the reflecting cone 28, the largest diameter of the reflecting cone is between 15 and 20 millimeters since the reflecting cone otherwise acts as an aperture of the optical system if the diameter is smaller. The crosssection of the reflecting cone 28 is convex or straight in order to reduce difficulties with optical alignment and to arrive at a total demagnification of between 2 and 3× at the face of the entry end 22 of the cylindrically shaped internal reflection element 12.

As shown in FIG. 2, in the case where the infrared radiation 20 from the source is converging, the contour of the surface of the reflecting cone 28 is preferably an ellipsoid segment 34 having ellipsoid foci $F_1$ at the original focal plane of the infrared radiation 20 from the source and $F_2$ at a point in space beside and forward of the reflecting cone, which acts effectively as a new source from which the radiation emanates. The length of the reflecting cone 28 is determined by the desired clear aperture for the infrared radiation 20 from the source. With regard to the reflecting toroid 30, infrared radiation impinged on the face of the entry end 22 of the cylindrically shaped internal reflection element 12 is desirably at normal incidence, that is, at 45° to the optical axis 18. Consequently, as shown in FIG. 2, the contour of the surface of the reflecting toroid 30 is preferably an ellipsoid segment 36 having as one ellipsoid focus the focus $F_2$ for the ellipsoid segment 34 of the reflecting cone 28 and as the other ellipsoid focus the point $F_3$ at or about the entry end 22 of the cylindrically shaped internal reflection element 12. The total magnification provided by the first optical means 14 equals $$\left( \frac{\overline{P_1 F_2}}{\overline{P_1 F_1}} \right) \times \left( \frac{\overline{P_2 F_3}}{\overline{P_2 F_2}} \right) \approx \frac{1}{2.5}.$$

Figure 8:
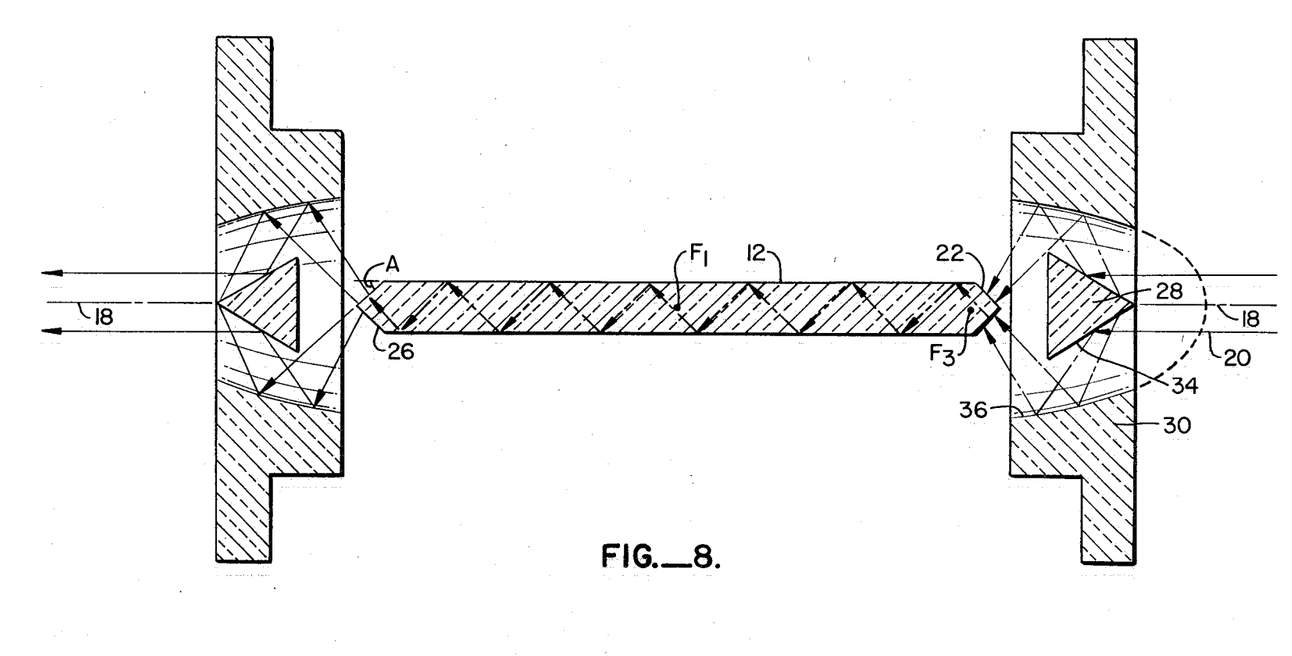
FIG. 8 is a schematic diagram of an alternative optical system in accordance with the invention included in the multiple internal reflection cell shown in FIG. 1.

In the case where the source infrared radiation is collimated, the reflecting cone 28 is preferably described by a parabolic surface of revolution, and the reflecting toroid 30 is preferably described by a cone surface of revolution, or vice versa as shown in FIG. 8. The ellipsoidal, or parabolic, surfaces can be approximated by the use of spherical surfaces or a combination of flat and spherical surfaces.

The same reflecting cone 28 and reflecting toroid 30 can be used for both sizes of the cylindrically shaped internal reflection element 12 listed in Table I. The frame for the optical system to be described later can preferably be adjusted in order to change from using the larger to smaller cylindrically shaped internal reflection element 12 and vice versa. Optical performance is not compromised in making this transition. The total diameter of the first optical means 14 is preferably less than 3½" in diameter in order to accommodate IR analyzer sample compartments with a floor to beam centerline dimension of 2".

Since different crystalline materials have different indexes of refraction, the first optical means 14 can be re-configured in order to optimize the infrared radiation throughput for each different cylindrically shaped internal reflection element 12. This is not deemed necessary, however, since the cone angle A of the face of the entry end 22 of the cylindrically shaped internal reflection element 12 can be changed in order to compensate for most index changes.

The second optical means 16 is preferably identical to the first optical means 14, although reversed in orientation. From a theoretical standpoint, the second optical means 16 can have a slightly different configuration than the first optical means 14 since misalignment and irregularities of mirror and crystal surfaces cause some scattering of infrared radiation at the exit end 26 of the cylindrically shaped internal reflection element 12. However, practical considerations such as ease of use and manufacturing cost dictate that the first and second optical means 14, 16 are preferably the same.

The combination of the convex cone mirror 28 and the concave toroidal mirror 30 brings the infrared radiation 20 from the source of an IR analyzer into focus at an average angle of A on the surface of the entry end 22 of the cylindrically shaped internal reflection element 12. A similar pair of mirrors included in the second optical means 16 at the exit end 26 of the cylindrically shaped internal reflection element 12 redirects the emerging infrared radiation towards the detector.

As shown in FIG. 1, the multiple internal reflection cell 10 further includes a tubular member 38 which contains the cylindrically shaped internal reflection element 12. The tubular member 38 preferably includes end flanges 40 and 42. Holes 44 and 46 are preferably provided in the respective end flanges 40 and 42 of the tubular member 38.

The cylindrically shaped internal reflection element 12 is mounted in the tubular member 38 with the entry end 22 of the element protruding through the hole 44 in the end flange 40 of the tubular member and with the exit end 26 extending through the hole 46 in the end flange 42 of the tubular member. The cylindrically shaped internal reflection element 12 is sealed into the tubular member 38 by means of O-ring seals 48 and 50 associated with the end flanges 40 and 42, respectively, of the tubular member 38.

The tubular member 38 included in the multiple internal reflection cell 10 with the O-ring seals 48 and 50 provides the means by which a sample is contained and remains in contact with the surface of the cylindrically shaped internal reflection element 12 and centers the element concentrically with the optical axis 18. The O-ring seal 48 preferably comprises an O-ring 52 which is wedged between a countersunk surface 54 of the end flange 40 of the tubular member 38 and an end plate 56 mounted to the end flange by means of screws 58. The O-ring seal 50 preferably has a configuration identical to the O-ring seal 48. The O-ring seals 48 and 50 are very easily made tight. Furthermore, since the O-ring seals 48 and 50 are close to the entry end 22 and exit end 26 of the cylindrically shape internal reflection element 12, little optical interference occurs.

A sample chamber 60 is formed by the region between the cylindrically shaped internal reflection element 12 and the tubular member 38 for containing a sample, such as a liquid or a solid in powder form. Since O-rings are preferably used for simply and effectively sealing the sample in the sample chamber 60, the effective sealing surface is small compared to the total sample area, resulting in minimal spectrum contribution of the O-rings. The use of O-rings permits high pressures to be handled. This allows for creating reactor chambers where both high pressures and temperatures can be accommodated without complex and difficult seals normally associated with known transmission cells. Sealing around a rod of crystalline material can be accomplished with Teflon (registered trademark) O-rings which have superior chemical inertness. The sample chamber 60 surrounding the cylindrically shaped internal reflection element 12 is configured to provide a free flow of sample so that the sample chamber fills without trapping bubbles and empties completely, leaving no pockets of residue sample.

Various configurations for the multiple internal reflection cell 10 are easily accommodated. One configuration is an open boat multiple internal reflection cell 10 shown in FIG. 1 with an open top which allows easily filling and/or emptying the cell. Another configuration is a stainless steel high pressure cell with low volume and Swagelok (registered trademark) type fittings so that the cell can be used as a flowthrough cell. Additionally, the configuration can be a Pyrex (registered trademark) cell with a glass tube removably disposed in a metal sheath for easy viewing of the sample about the cylindrically shaped internal reflection element 12, as well as easy filling and emptying. This latter cell can have a relatively large volume in order to assure freedom from air bubbles about the cylindrically shaped internal reflection element 12.

Referring again to FIG. 1, the multiple internal reflection cell 10 includes an optical bench or frame 62 which provides the mechanical structure for securing the first and second optical means 14, 16 and the cylindrically shaped internal reflection element 12 along the common optical axis 18 at prescribed distances from each other and from the optics of an IR analyzer in order to assure optimum infrared radiation throughput in a repeatable fashion when the cell is incorporated into the sample compartment of an FTIR spectrophotometer. The optical bench 62 comprises a connecting or top plate 64, a first lens bracket 66 for the first optical means 14, a second lens bracket 68 for the second optical means 16, and a sample holding bracket 70.

The connecting plate 64 provides the means for maintaining mechanical (and optical) separation and alignment of the first optical means 14, cylindrically shaped internal reflection element 12, and second optical means 16. The connecting plate 64 can allow for two position ranges of the first lens bracket 66 and/or second lens bracket 68 dependent upon the size of the cylindrically shaped internal reflection element 12 listed in Table I. The outermost positions can be used for the larger size crystal (Crystal I). The innermost positions can be used for the smaller size crystal (Crystal II). The connecting plate 64 preferably has two large cut-out areas 72 in order to provide working space for various configurations of the multiple internal reflection cell 10 and/or associated plumbing and/or other fixturing of the cell. The cut-out areas 72 also provide access to lock screws 76 in order to secure the multiple internal reflection cell 10 within the sample compartment of an FTIR spectrophotometer.

The first lens bracket 66 is fastened to the connecting plate 64 by means of a screw 78. A slight amount of play is allowed in order to provide for adjustment during alignment. Once aligned, the first lens bracket 66 is firmly secured to the connecting plate 64 with no play allowed.

The first optical means 14 fits into the first lens bracket 66 with a tight tolerance slip fit in order to allow the first optical means to be moved into position during alignment. Once the position which optimizes infrared radiation throughput is established, the first optical means 14 is firmly secured in the first lens bracket 66 by means of a clamping screw 80 which causes the first lens bracket to lock-down around the circumference of the first optical means 14. The second lens bracket 68 preferably has a configuration identical to the first lens bracket 66.

The sample holding bracket 70 provides for highly repeatable placement of the cylindrically shaped internal reflection element 12 onto the optical bench 62. A slight amount of play is provided in order to assure optical alignment of the cylindrically shaped internal reflection element 12 with the first and second optical means 14, 16. This play is removed after alignment when the sample holding bracket 70 is firmly secured to the connecting plate 64. The sample holding bracket 70 preferably has at least one tight tolerance pin (not shown) in the cradle for the tubular member 38 in order to assure highly repeatable replacement of the cylindrically shaped internal reflection element 12. Two pins can be used for assuring repeatability. The tubular member 38 is clamped in the sample holding bracket 70 by means of thumb screws 82 for firmly securing the tubular member onto the sample holding bracket without using tools.

A baseplate 84 provides the mechanism which enables optical alignment between the optical bench 62 and the optics of an FTIR spectrophotometer and secures the multiple internal reflection cell 10 to the sample compartment floor plate of the IR analyzer. The baseplate 84 is preferably connected to the connecting plate 64 by means of a standoff 86. Gross height adjustment is provided by the standoff 86 which has a length for approximately establishing the proper distance of the optical bench 62 to the floor of an FTIR spectrophotometer sample compartment. The standoff 86 can be exchanged in order to allow the multiple internal reflection cell 10 to be incorporated into different IR analyzers with relative ease. Kinematic (3-point) adjustment is provided by the adjusting screws 74 having swivel pads in order to allow the optical bench 62 to gimbal so as to cause the optical axis 18 of the multiple internal reflection cell 10 to be coaxial with the optical axis or center line of the FTIR spectrophotometer. This is desirable since the axis of the infrared radiation 20 from the source of an IR analyzer does not always traverse the sample compartment perpendicular to the side wall geometry of the compartment (i.e., it is not square). Rather, the infrared radiation 20 from the source usually has a skew path. Side-to-side alignment is allowed by providing a slight amount of play in the hole through the baseplate 84 for the lock screws 76 which secure the multiple internal reflection cell 10 to the floor of the FTIR spectrophotometer sample compartment. Sufficient play allows the multiple internal reflection cell 10 to be slid on the floor of the IR analyzer sample compartment in order to optimize infrared radiation throughput.

Since IR analysis is nondestructive, sampling can be accomplished by setting up a loop which draws a sample from a reaction vessel or from a process stream, passes the sample through the sample chamber 60 and returns the sample to the vessel or stream. Accordingly, attached to the bottom of the optical bench 62 is preferably a sample handling system (not shown). The sample handling system can vary from application to application. A typical sample handling system includes valves, filters, a pump, and safety drains.

The multiple internal reflection cell 10 is configured to be highly repeatable and easy to use. A procedure for using the multiple internal reflection cell 10 is preferably as follows.

Initially, the multiple internal reflection cell 10 is optically aligned, and the final infrared radiation throughput at the end of the alignment procedure is measured. Next, a background is sampled with the empty multiple internal reflection cell 10 as just aligned (i.e., with the cell properly aligned in the sample compartment of the IR analyzer without a sample or blank in the cell). The resultant background data is saved in a background file. Then, the multiple internal reflection cell 10 is filled with a reference or blank. Next, the blank is sampled, and the resultant blank data is saved in a blank file. The blank data can be plotted. Thereafter, the multiple internal reflection cell 10 is cleaned by either removing the cell, emptying the contents, and flushing with appropriate solvent (and drying with dry air) or simply flushing the cell with the sample. (If the cell must be disassembled for cleaning, refocusing of the first and second optical means 14, 16 is needed unless the cylindrically shaped internal reflection element 12 is replaced to the identical location in the cell.) Subsequently, if the multiple internal reflection cell 10 has been removed, the cell is replaced, and the infrared radiation throughput of the empty cell is checked in order to assure that the cell has been aligned properly. (The throughput should be the same as that measured initially.) Next, the multiple internal reflection cell 10 is filled with the sample. The sample is sampled, and the resultant sample data is saved in a sample file. The sample data is thereafter plotted versus the background. Then, a difference factor is determined which represents the amount of the blank in the sample under examination. The difference factor is multiplied by the blank file before subtraction in order to vary the amount of blank subtracted from the sample file. When an appropriate difference factor has been selected, the difference (sample) minus (factor) times (blank) is obtained in order to yield a spectrum which can be displayed and/or plotted.

The operation of the multiple internal reflection cell 10 is based on the well-defined theory of total internal reflection as applied to infrared spectroscopy. The technique is generally referred to as internal reflection spectroscopy and is described in the book *Internal Reflection Spectroscopy* by N. J. Harrick and in the ASTM reprint ASTM Designation: E573-81, "Standard Practices for Internal Reflection Spectroscopy." Calculations for the approximate number of internal reflections can be made using equations for internal reflection elements which appear in ASTM. Since only flat-plate internal reflection elements are discussed in that publication, however, the equations, when used for cylindrically shaped internal reflection elements, are at best approximate. Although the various rod crystal cylindrically shaped internal reflection elements 12 shown in FIG. 3, as well as the tubular crystal element shown in FIG. 4, are not discussed in either of the publications referenced, many of the concepts disclosed in the two referenced publications are applicable to the operation of the multiple internal reflection cell 10.

For the purpose of analysis, a two-dimensional model is used. As long as the multiple internal reflection cell 10 is well-aligned, the two-dimensional model provides a basis for explaining the theory which underlies the operation of the cell.

The two-dimensional model used is described by taking a plane along the optical axis 18. The plane for simplicity is chosen as the vertical plane, and, therefore, the sectional side view shown in FIG. 2 graphically represents the model.

The infrared radiation 20 from the source can be converging to a focus either at a point near the center of the sample compartment or near the left side of the compartment. Most discussions herein refer to those IR analyzers with a center focus even though the concept applies equally well with a side focus. The infrared radiation 20 from the source is assumed to be a center focus beam with a circular cross-section.

The infrared radiation 20 from the source reflects off the surface of the reflecting cone 28 onto the reflecting toroid 30 surface where it is reflected onto the face of the entry end 22 of the cylindrically shaped internal reflection element 12. The infrared radiation enters the cylindrically shaped internal reflection element 12 at normal or near normal incidence and is transmitted through the crystalline material of the element until the radiation reaches the cylindrical surface of the element where the radiation is internally reflected at an equal and opposite angle toward the cylindrical surface opposite the initial reflection point. As the infrared radiation is internally reflected, the radiation is encoded with information about the absorptive characteristics of the sample with which the cylindrical surface is in contact.

The infrared radiation continues to be internally reflected along the full length of the cylindrically shaped internal reflection element 12 until the radiation reaches the exit end 26 of the element, whereupon the angle of incidence is near normal, causing the radiation to be largely transmitted through the face and onto the surface of the reflecting toroid of the second optical means 16. From there the infrared radiation is reflected onto the reflecting cone of the second optical means 16 and then is reflected on towards the detector optics and/or detector.

Due to alignment tolerances and/or manufacturing variations, along with the fact that the infrared radiation 20 from the source is not converging exclusively toward a point along the optical axis 18, the radiation is not entirely in the vertical plane of the two-dimensional model. Consequently, the infrared radiation is not totally reflected through the cylindrically shaped internal reflection element 12 to the opposite cylindrical surface. As a result, the infrared radiation does not remain in the same plane after the internal reflection as before the reflection. This causes the infrared radiation to have a corkscrew type zig-zag propagation from one end of the cylindrically shaped internal reflection element 12 to the other. As the infrared radiation emerges from the exit end 26 of the cylindrically shaped internal reflection element 12, the radiation is not emitted in a purely radial direction relative to the optical axis 18.

The effect is to cause the angle(s) of incidence of the infrared radiation to have a slightly changed angle than theorized in the ideal case for each reflection at the cylindrical surface and for the radiation emanating from the exit end 26 of the cylindrically shaped internal reflection element 12 to be somewhat more defocused than in the ideal case. As a practical sampling method, the effect is of little significance with the multiple internal reflection cell 10 unless there is significant misalignment, in which case, however, the signal-to-noise ratio is impaired so that the need for re-alignment is apparent.

Four solutions of acetone in water were prepared for analysis by the multiple internal reflection cell 10. The acetone concentrations were 0.2%, 2%, 5%, and 10%, thereby giving a 50-fold range of concentrations.

A background was initially run, and a background file was created containing the spectrum of the empty multiple internal reflection cell 10. This background file was created for being automatically subtracted from each sample run for subtracting out the atmosphere and crystal spectra.

Pure water was used as the blank. A pure water spectrum was run and stored in a file for subtraction. The four samples were then run and plotted. Five-minute FTIR spectrophotometer runs (300 scans) were made with a Nicolet 5-MX spectrophotometer at 4 cm$^{-1}$ resolution.

Figure 5:
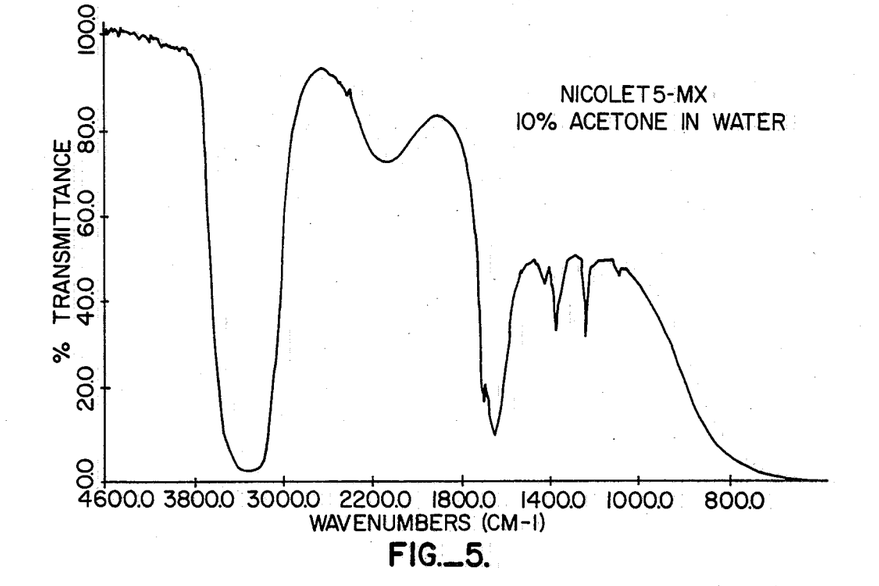
FIG. 5 shows a raw spectrum of 10% acetone in water obtained with the multiple internal reflection cell shown in FIG. 1 incorporated into a commercially available FTIR spectrophotometer.

FIG. 5 shows the raw spectrum of 10% acetone in water. Next, the subtraction of water was performed, requiring (on the Nicolet 5-MX spectrophotometer) the manual choice of the proper difference factor (percentage or reference to be subtracted). The proper factor was generally zeroed in on after five or fewer plots.

Figure 6:
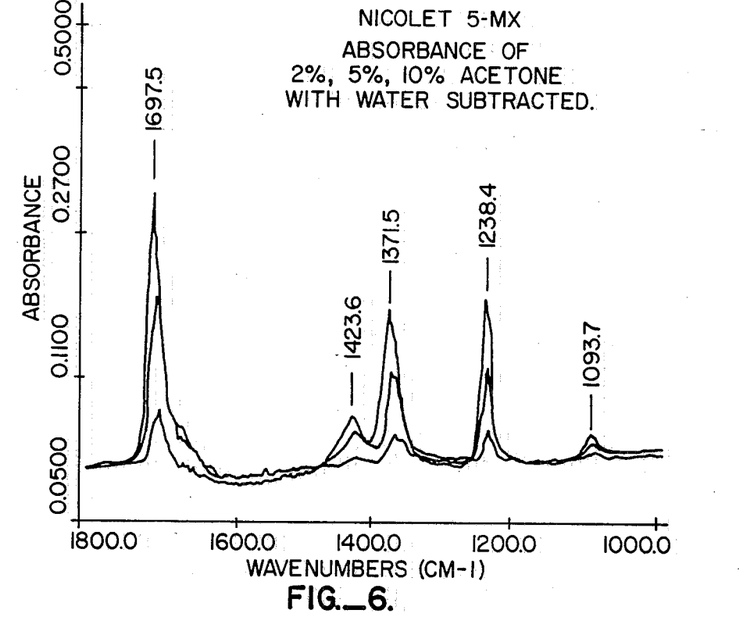
FIG. 6 shows normalized spectra of 2%, 5%, and 10% acetone in water obtained with the multiple internal reflection cell shown in FIG. 1 incorporated into a commercially available FTIR spectrophotometer.
Figure 7:
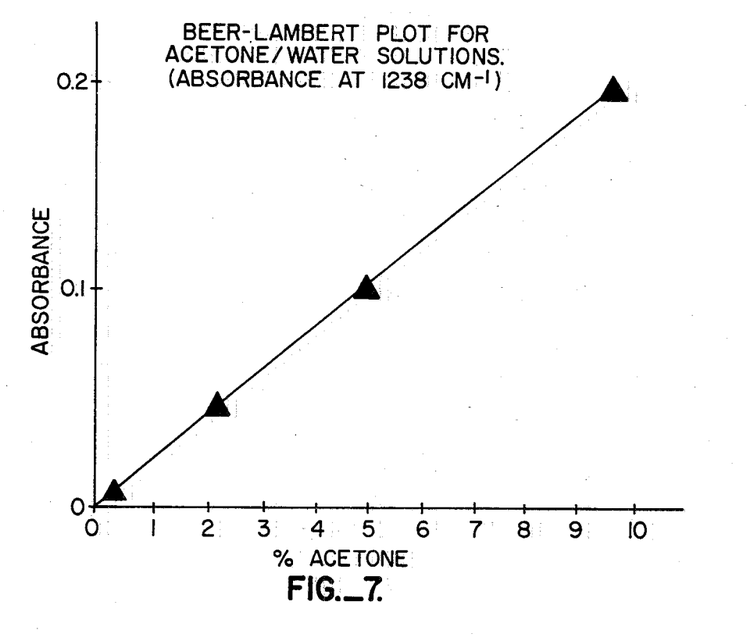
FIG. 7 is a Beer-Lambert plot for aqueous acetone solutions obtained with the multiple internal reflection cell shown in FIG. 1 incorporated into a commercially available FTIR spectrophotometer.

FIG. 6 shows the 2%, 5%, and 10% acetone traces after subtraction of water, each using the proper difference factor. FIG. 7 shows that the points for the four samples lie on a straight line passing through the origin.

The multiple internal reflection cell 10 can be incorporated into various known commercially available IR analyzers by being configured to be firmly attached to the sample platform and filled and emptied without moving the cell. Hence, the multiple internal reflection cell 10 provides highly reproducible qualitative and quantitative data.

The multiple internal reflection cell in accordance with the invention, when used with a computerized spectrophotometer (usually a FTIR) provides a highly accurate, repeatable sampling method for solutions of the type described. Although a computerized spectrophotometer is not necessary for the procedure, computers facilitate use in quantitative IR analysis.

The multiple internal reflection cell in accordance with the invention is not limited to analyzing aqueous solutions. With 10 reflections at a 45° angle of incidence, path lengths of 8 to 12 micrometers are routinely achieved. This means that the multiple internal reflection cell in accordance with the invention provides a highly repeatable liquid cell with a path length not easily achieved by transmission cells and, therefore, is useful with other highly absorbing solvent solutions.

The foregoing description is offered primarily for purposes of illustration. While a variety of embodiments has been disclosed, it will be readily apparent to those skilled in the art that numerous other modifications and variations not mentioned above can still be made without departing from the spirit and scope of the invention as claimed below.

What is claimed is:

1. Optics in combination with a cylindrically shaped internal reflection element forming an optical system for a multiple internal reflection cell, the optics comprising:
   first optical means in the form of reflaxicon optics responsive to radiation from collimated to f number 1 from a source of infrared radiation for focusing the radiation on an entry end of the element at an angle of incidence conducive to transfer of substantially all the radiation to the element;
   the radiation transferred to the element being multiply internally reflected through the element from the entry end to an exit end of the element; and
   second optical means in the form of reflaxicon optics responsive to substantially all radiation emanating from the exit end of the element for transmitting the radiation in a pattern for optimum throughput to a detector.

2. The optics of claim 1 wherein the infrared radiation from the source is converging and wherein the first optical means comprises a first reflecting cone and a first reflecting toroid mounted with respect to one another so that substantially all radiation from the source is transferred to the element and wherein the second optical means comprises a second reflecting cone and a second reflecting toroid mounted with respect to one another so that substantially all radiation emanating from the element is transferred towards the detector in a diverging pattern, the contours of the surfaces for the respective first and second reflecting cones and the associated first and second reflecting toroids being segments of revolution where the segments are defined as off-axis ellipsoids.

3. The optics of claim 2 wherein the element comprises a rod of crystalline material consisting of one of the materials ZnSe, Ge, Si sapphire, AgBr, AgCl, KRS-5, HDPE, and ZnS.

4. The optics of claim 3 wherein the element comprises a rod of ZnSe having a 90° cone-shaped entry end and a 90° cone-shaped exit end.

5. The optics of claim 3 wherein the element comprises a tube of ZnSe having a 45° angled entry end and a 45° angled exit end.

6. The optics of claim 1 wherein the infrared radiation from the source is collimated and wherein the first optical means comprises a first reflecting cone and a first reflecting toroid mounted with respect to one another so that substantially all radiation from the source is transferred to the element and wherein the second optical means comprises a second reflecting cone and a second reflecting toroid mounted with respect to one another so that substantially all radiation emanating form the element is transferred towards the detector in a collimated pattern, the contours of the surfaces for the respective first and second reflecting cones and the associated first and second reflecting toroids being segments of revolution where the segments are defined as cones and off-axis paraboloids, respectively.

7. The optics of claim 6 wherein the element comprises a rod of crystalline material consisting of one of the materials ZnSe, Ge, Si, sapphire, AgBr, AgCl, KRS-5, HDPE, and ZnS.

8. The optics of claim 7 wherein the element comprises a rod of ZnSe having a 90° cone-shaped entry end and a 90° cone-shaped exit end.

9. The optics of claim 7 wherein the element comprises a tube of ZnSe having a 45° angled entry end and a 45° angled exit end.

10. The optics of claim 1 wherein the element comprises a rod of crystalline material consisting of one of the materials ZnSe, Ge, Si, sapphire, AgBr, AgCl, KRS-5, HDPE, and ZnS.

11. The optics of claim 10 wherein the element comprises a rod of ZnSe having a 90° cone-shaped entry end and a 90° cone-shaped exit end.

12. The optics of claim 10 wherein the element comprises a tube of ZnSe having a 45° angled entry end and a 45° angled exit end.

13. The optics of claim 1 wherein the throughput is at least 15% of the open beam throughput.

14. A multiple internal reflection cell for containing a fluid sample having a characteristically high infrared absorbency during infrared spectroscopy, wherein infrared radiation from a collimated to f number 1 source of infrared radiation is passed through the cell to an infrared detector in the presence of the sample, the cell comprising:
a tubular member positioned between the source and the detector;
a cylindrically shaped internal reflection element sealed in the tubular member, the element having an entry end and an exit end;
the sample being contained in a region between the tubular member and the element within the tubular member;
first optical means in the form of reflaxicon optics responsive to the collimated to f number 1 radiation from the source for focusing the radiation of the entry end of the element at an angle of incidence conductive to transfer of substantially all the radiation to the element; and
second optical means in the form of reflaxicon optics responsive to substantially all radiation emanating from the exit end of the element for transmitting the radiation towards the detector in a radiation pattern for optimum throughput to the detector.

15. The multiple internal reflection cell of claim 14 wherein the infrared radiation from the source is converging and wherein the first optical means comprises a first reflecting cone and a first reflecting toroid mounted with respect to one another so that substantially all radiation from the source is transferred to the element and wherein the second optical means comprises a second reflecting cone and a second reflecting toroid mounted with respect to one another so that substantially all radiation emanating from the element is transferred towards the detector in a diverging pattern, the contours of the surfaces for the respective first and second reflecting cones and the associated first and second reflecting toroids being segments of revolution where the segments are defined as off-axis ellipsoids.

16. The multiple internal reflection cell of claim 15 wherein the element comprises a rod of ZnSe having a 90° cone-shaped entry end and a 90° cone-shaped exit end.

17. The multiple internal reflection cell of claim 14 wherein the infrared radiation from the source is collimated and wherein the first optical means comprises a first reflecting cone and a first reflecting toroid mounted with respect to one another so that substantially all radiation from the source is transferred to the element and wherein the second optical means comprises a second reflecting cone and a second reflecting toroid mounted with respect to one another so that substantially all radiation emanating from the element is transferred towards the detector in a collimated pattern, the contours of the surfaces for the respective first and second reflecting cones and the associated first and second reflecting toroids being segments of revolution where the segments are defined as cones and off-axis paraboloids, respectively.

18. The multiple internal reflection cell of claim 17 wherein the element comprises a rod of ZnSe having a 90° cone-shaped entry end and a 90° cone-shaped exit end.

19. The multiple internal reflection cell of claim 14 wherein the element comprises a rod of ZnSe having a 90° cone-shaped entry end and a 90° cone-shaped exit end.

20. The multiple internal reflection cell of claim 14 wherein the throughput is at least 15% of the open beam throughput.

21. In a multiple internal reflection cell comprising input folding and condensing optics, a cylindrically shaped internal reflection element, a sample chamber, output collecting and directing optics, and alignment and supporting means, the improvement comprising:
first optical means of focusing reflaxicon configuration including a first reflecting cone and a first reflecting toroid having reflecting surfaces whose contours are surfaces of revolution;
a cylindrically shaped internal reflection element consisting of infrared radiation transmitting material having a cone-shaped entry end whose angle is established for effecting a desired penetration of radiation into a sample in contact with the surface of the element for each internal reflection along the element and a cone-shaped exit end whose angle is established for matching the radiation from the element to second optical means in order to assure optimum radiation collection by the second optical means, the surfaces of the element being polished in order to assure total internal reflection;
a member for enclosing the element, a sample chamber being formed between the element and the member for containing a sample around and in contact with the element;

second optical means of reflaxicon configuration including a second reflecting cone and a second reflecting toroid having reflecting surfaces whose contours are surfaces of revolution; and optical bench means for optically aligning the first optical means, the element, and the second optical means.

22. The multiple internal reflection cell of claim 21 wherein converging infrared radiation from a source is impinged on the cell and wherein the first and second optical means are configured for transferring the radiation towards a detector in a diverging pattern, the contours of the surfaces for the respective first and second reflecting cones and the associated first and second reflecting toroids being segments of revolution where the segments are defined as off-axis ellipsoids.

23. The multiple internal reflection cell of claim 21 wherein collimated infrared radiation from a source is impinged on the cell and wherein the first and second optical means are configured for transferring the radiation towards a detector in a collimated pattern, the contours of the surfaces for the respective first and second reflecting cones and the associated first and second reflecting toroids being segments of revolution where the segments are defined as cones and off-axis paraboloids, respectively.

24. The multiple internal reflection cell of claim 21, further comprising first and second 0-ring seal means at the respective entry end and exit end of the element for sealing the element within the member.

25. The multiple internal reflection cell of claim 21 wherein the member includes an opening in the member to provide access to the interior of the member, and further comprising first and second O-ring seal means at the respective entry end and exit of the element for sealing the element within the member.

26. The multiple internal reflection cell of claim 21 wherein the member includes stainless stell tube means for withstanding high pressures and temperatures, the tube means having a port means for filling, emptying, and cleaning, and further comprising first and second O-ring seal means at the respective entry end and exit end of the element for sealing the element within the tube means.

27. The multiple internal reflection cell of claim 21 wherein the member includes glass tube means for providing an inert sample chamber, the glass tube means being removably disposed in a metal sheath, and further comprising first and second 0-ring seal means at the respective entry end and exit end of the element for sealing the element within the glass tube means.

28. The multiple internal reflection cell of claim 21, further comprising adjusting means including screws having swivel pads for gimbaling the optical bench means in order to assure optical alignment of the cell with respect to the optical axis of infrared radiation from a source to a detector.

29. The multiple internal reflection cell of claim 21 wherein the optical bench means includes first and second lens bracket means for adjustably positioning the respective first and second optical means in order to optimize throughput of infrared radiation.

30. The multiple internal reflection cell of claim 29 wherein the optical bench means includes connecting plate means for adjustably positioning the respective first and second lens bracket means.

31. A method for internal reflection infrared spectroscopy, comprising the steps of:

sampling a background using an empty multiple internal reflection cell using reflaxicon optic means for optically coupling a source of collimated to f number 1 infrared radiation through a cylindrically shaped internal reflection element to a detector with a throughput at least 15% of the open beam throughput;

storing the background data in a background file;

filling the cell with a blank material;

sampling the blank material using the cell filled with the blank material;

storing the blank data in a blank file;

purging the blank material from the cell;

filling the cell with a sample;

sampling the sample using the cell filled with the sample;

storing the sample data in a sample file;

determining a difference factor which represents the percent amount of the blank material in the sample; and performing a subtraction of the background and the percent amount of blank material from the sample so as to yield a spectrum of the difference.

32. The method of claim 31 wherein the source radiation is converging and wherein the steps of sampling comprise impinging the source radiation on a first reflection cone, reflecting the radiation off the first reflecting cone onto a first reflecting toroid so that substantially all source radiation is transferred to an entry end of the element, reflecting the radiation through the element to an exit end of the element, impinging the radiation emanating from the exit end of the element on a second reflecting toroid, reflecting the radiation off the second reflecting toroid onto a second reflecting cone so that substantially all radiation emanating from the element is transferred towards the detector in a diverging pattern, the contours of the surfaces for the respective first and second reflecting cones and the associated first and second reflecting toroids being segments of revolution where the segments are defined as off-axis ellipsoids.

33. The method of claim 31 wherein the source radiation is collimated and wherein the steps of sampling comprise impinging the source radiation on a first reflecting cone, reflecting the radiation off the first reflecting cone onto a first reflecting toroid so that substantially all source radiation is transferred to an entry end of the element, reflecting the radiation through the element to an exit end of the element, impinging the radiation emanating from the exit end of the element on a second reflecting toroid, reflecting the radiation off the second reflecting toroid onto a second reflecting cone so that substantially all radiation emanating from the element is transferred towards the detector in a collimated pattern, the contours of the surfaces for the respective first and second reflecting cones and the associated first and second reflecting toroids being segments of revolution when the segments are defined as cones and off-axis paraboloids, respectively.

* * * * *

Disclaimer and Dedication 4,595,833—Donald W. Sting, New Canaan, Conn. MULTIPLE INTERNAL REFLECTION CELL OPTICAL SYSTEM FOR USE IN INFRARED SPECTROPHOTOMETRY OF LIQUID AND FLUIDIZED SAMPLES. Patent dated June 17, 1986. Disclaimer and Dedication filed May 18, 2001, by the assignee, Spectra-Tech, Inc.

Hereby disclaims and dedicates to the Public all claims and entire term of said patent.
*(Official Gazette, July 31, 2001)*